(12) United States Patent
Volker et al.

(10) Patent No.: US 7,260,482 B2
(45) Date of Patent: Aug. 21, 2007

(54) ULTRASONIC CHARACTERIZATION OF HIGH CONCENTRATION PARTICLES

(75) Inventors: Arno Willem Frederik Volker, Delf (NL); Frédérique José Paul Christian Marie Ghislain Verhelst, Hoofddorp (NL); Rolf Willem Bartstra, Rotterdam (NL)

(73) Assignee: Nederlandse Organisatie Voor Toegepast-Natuurwetenschappelijk Onderzoek Tno, Delft (NL)

( * ) Notice: Subject to any disclaimer, the term of this patent is extended or adjusted under 35 U.S.C. 154(b) by 0 days.

(21) Appl. No.: 10/516,194

(22) PCT Filed: May 27, 2003

(86) PCT No.: PCT/NL03/00393

§ 371 (c)(1),
(2), (4) Date: Jun. 20, 2005

(87) PCT Pub. No.: WO03/102550

PCT Pub. Date: Dec. 11, 2003

(65) Prior Publication Data

US 2006/0058981 A1    Mar. 16, 2006

(30) Foreign Application Priority Data

May 30, 2002    (NL) .................................. 1020714

(51) Int. Cl.
  *G01N 15/00*    (2006.01)
  *G01N 15/02*    (2006.01)
  *G01N 15/06*    (2006.01)
  *G01N 29/02*    (2006.01)

(52) U.S. Cl. .................. 702/22; 702/190; 73/61.75; 73/602; 73/646

(58) Field of Classification Search .................. 702/22, 702/190, 23, 25–26, 189; 73/602, 645–648
See application file for complete search history.

(56) References Cited

U.S. PATENT DOCUMENTS 6,481,268 B1 * 11/2002 Povey et al. ................ 73/61.75

* cited by examiner

*Primary Examiner*—Hal Wachsman
*Assistant Examiner*—Sujoy Kundu
(74) *Attorney, Agent, or Firm*—Norris, McLaughlin & Marcus (57) ABSTRACT

A method for characterizing a suspension with particles floating therein, which method comprises the steps of generating an acoustic actuation signal and registering an acoustic reflected signal. Further, a first dataset is calculated on the basis of the reflected signal, the dataset containing information which represents an autocorrelation function as a function of time of the reflected signal. Thereupon, first datasets are combined into a second, cumulated dataset, which represents a sum of the autocorrelation functions which correspond with the first datasets. Finally, a representation of a particle size distribution is determined by solving this representation from an expression for the second, cumulated dataset in terms of the representation of a particle size distribution.

8 Claims, 7 Drawing Sheets

ULTRASONIC CHARACTERIZATION OF HIGH CONCENTRATION PARTICLES

The invention relates to a method for characterizing a suspension with particles floating therein, which method comprises the steps of
performing a series of measurements, wherein each measurement comprises the substeps of
generating an acoustic actuation signal in the suspension using a transmitter,
registering an acoustic reflected signal coming from the suspension as a result of the actuation signal,
wherein the method further comprises the step of
determining a representation of a particle size distribution based on composite information of reflected signals from the measurements.

Such a method is known from the European Patent Publication No. 0801305 A. In the known method, using the transmitter, an acoustic signal is generated in a suspension, which flows through a channel. This signal has an interaction with the particles in the suspension, after which a receiver registers a reflected signal. Of the registered signal, the maximum amplitude is determined. This maximum amplitude is related to the magnitude of the particle that caused the reflected signal and the intensity of the sound beam at the location of the particle. By the use of sound waves, the measuring method is robust to contamination and any precipitation on the transmitter and the receiver. This type of measurement is repeated a number of times. On the basis of a classification of the maximum amplitudes of the reflected signals, a particle size distribution is determined.

For the accuracy of the measurement, it is important that not more than one particle makes a contribution to a reflected signal.

However, with increasing numbers of particles per unit of volume, that is, with increasing concentrations of particles in the suspension, more particles can make a contribution to the reflected signal in a measurement. This gives rise to a systematic error in the determination of the particle size distribution. Only the contribution of the particle that causes the greatest amplitude in the reflected signal is taken into account in the interpretation of the signal. The contribution of one or more other particles is ignored. As a consequence, the particle size distribution has a systematic error and other properties derived therefrom, such as, for instance, the particle concentration, that is, the amount of particles per unit of volume, cannot be accurately determined.

Reduction of the chance that more than one particle makes a contribution to the reflected signal is possible by minimizing the measurement volume, that is, the volume in the beam of the actuation signal, within which particles may be located that make a contribution to the reflected signal. The measurement volume can be reduced by narrowing the beam of the actuator. At a given bandwidth of the signal, which in turn is limited by the geometry and the dimensions of the transmitter, the possibilities of narrowing the beam are limited, however.

The invention contemplates a method of the type mentioned in the opening paragraph hereof, in which the disadvantage mentioned can be avoided. The invention contemplates providing a method in which a reliable and accurate determination of the representation of the particle size distribution of the particles in the suspension is possible also at relatively high particle concentrations. To that end, the method according to the invention is characterized in that it further comprises the step of
calculating for each measurement a first dataset on the basis of the reflected signal, wherein the dataset contains information which represents an autocorrelation function as a function of time of the reflected signal, and wherein the step of determining the representation of a particle size distribution comprises the two substeps of
combining the first datasets into a second, cumulated dataset, which represents a sum of the autocorrelation functions corresponding to the first datasets, and
solving the representation of a particle size distribution from an expression for the second, cumulated dataset in terms of the representation of a particle size distribution.

By calculating an autocorrelation function of the reflected signal, information is gathered of all particles that have contributed to the reflected signal. This involves, for instance, the reflected signal, regarded as a function of time, being multiplied at any time by the same function, while the temporal argument of one of the two functions is shifted over a first time interval. This product is subsequently integrated over a second, fixed time interval. The information from this calculation is obtained in the form of a first dataset and represents an autocorrelation function of the reflected signal or a function which contains the same information, such as, for instance, the power spectrum of the reflected signal. In this step of the method, of each reflected signal, from the measurement, a first dataset is determined of that reflected signal.

By combining the datasets obtained in the above-mentioned manner, such that the sum of the autocorrelation functions corresponding with the datasets is formed, a second, cumulated dataset is obtained. In this way, a representation is effected of all pulses in the reflected signals, of which a first dataset has been determined. Also the contribution of a particle where the maximum amplitude of the pulse caused by that particle is less than the maximum amplitude of the pulse caused by another particle has been taken into account here. The reason for this is that this information is not lost in determining the autocorrelation in the measured reflected signal. This in contrast with the known method from the European Patent Publication No. 0801305 A, in which only a representation is obtained of the maximum amplitude of the pulses in a reflected signal.

By comparing the thus obtained cumulative dataset with an expression for the cumulative dataset in terms of the particle size distribution, the particle size distribution is solved. This particle size distribution can serve as a basis for obtaining supplemental information with regard to the particles in the suspension, such as, for instance, the particle concentration.

The expression for the cumulative dataset is implemented as a dataset which comprises an integral representation in which an analytical model is included which gives a description of the scatter of sound waves by the particles in the suspension as a function of the diameter of the particles, the frequency of the actuation signal, and the characteristics of the transducer. Upon discretization of the expression, a matrix equation is obtained which can be solved, for instance, with a least squares method. It is clear to the skilled person that other solving methods are also applicable.

The method for characterizing a suspension with particles floating therein can also be applied advantageously in situations involving different types of particles, such as particles of different materials. To that end, in the above-mentioned integral representation, analytical models are included describing the scatter by each of the different types of particles. Moreover, the integral representation contains the particle size distributions of the different types of particles, so that these particle size distributions can be solved from the matrix equations with a block structure that results.

Not every registered reflected signal needs to be part of a measurement in the meaning in which that word is used here. For instance, some reflected signals may not be of interest for further processing in connection with noise or disturbances. The registration mentioned thus does not form a part of a measurement as meant in this application.

The invention will be further elucidated on the basis of an exemplary embodiment which is represented in the drawings. In the drawings.

Figure 1:
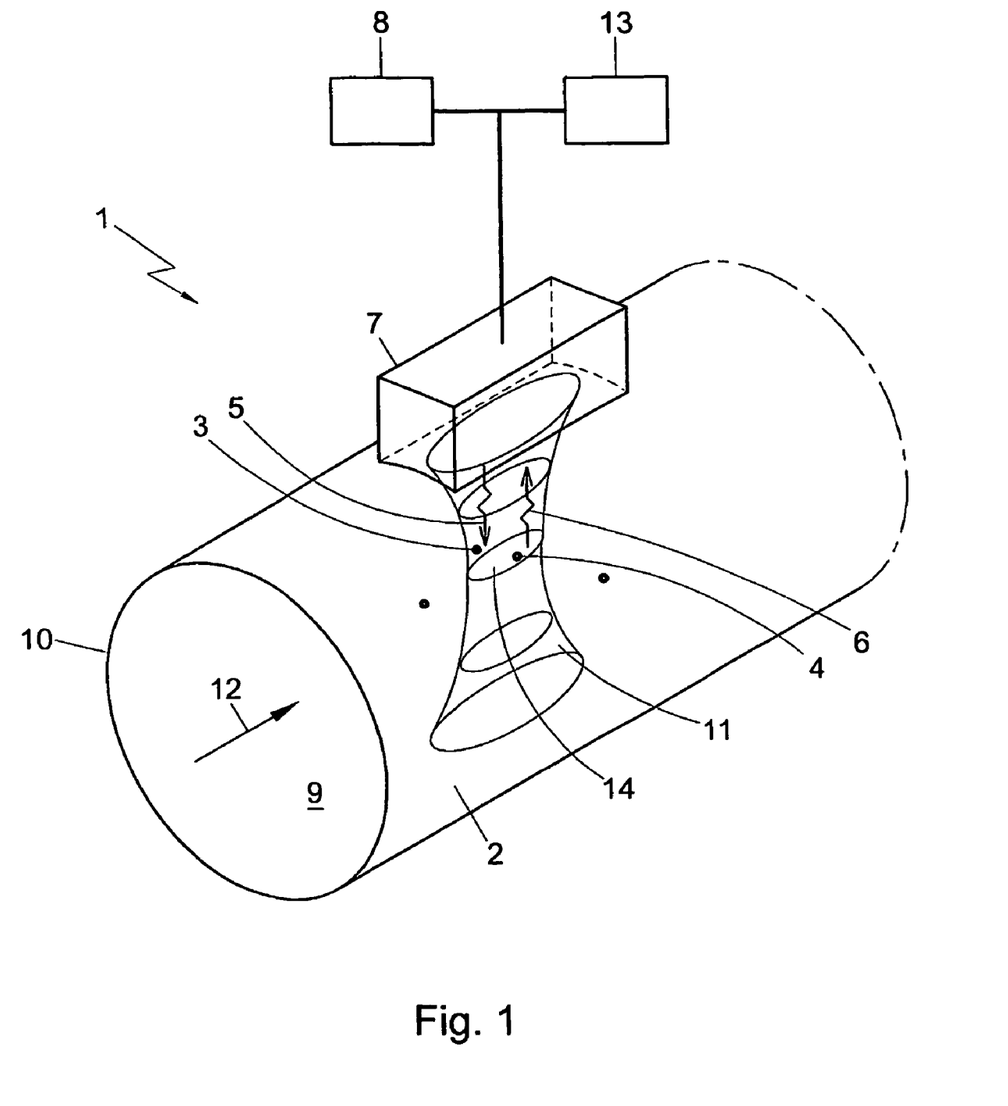
FIG. 1 is a schematic perspective view of a measuring device according to the invention.

FIG. 1 represents a measuring device 1 which comprises a cylinder-shaped channel 2. Present in the channel is a liquid with particles 3, 4 floating therein. The small particles are represented symbolically with dots. The suspension 9 can comprise, for instance, water or oil with sand particles, or water with oil particles. This suspension 9 flows, for instance, in the direction 12 indicated with the arrow. In the wall 10 of the channel 2, an ultrasound transducer 7 is included, which functions consecutively as transmitter and receiver. The transducer 7 is electrically connected with a signal generator 8 for the actuation of signals and with a arithmetic unit 13 for processing and interpreting measured data.

In operation, the signal generator 8 generates an electrical signal which the transducer 7, coupled thereto, converts as a transmitter to an acoustic actuation signal 5. The actuation signal can be a random transient function of time, such as, for instance, a broadband pulse or a sinusoidal signal such as a frequency sweep. The beam geometry of the transmitter is also random, such as, for instance, a focused beam. In the preferred embodiment, the actuation signal 5 has a largest possible bandwidth, for instance of 10-40 MHz. When this signal 5 is coupled into the suspension 9, a sound beam 11 is formed which, adjacent the locus, in lateral direction by approximation has a Gaussian intensity profile.

Figure 2:
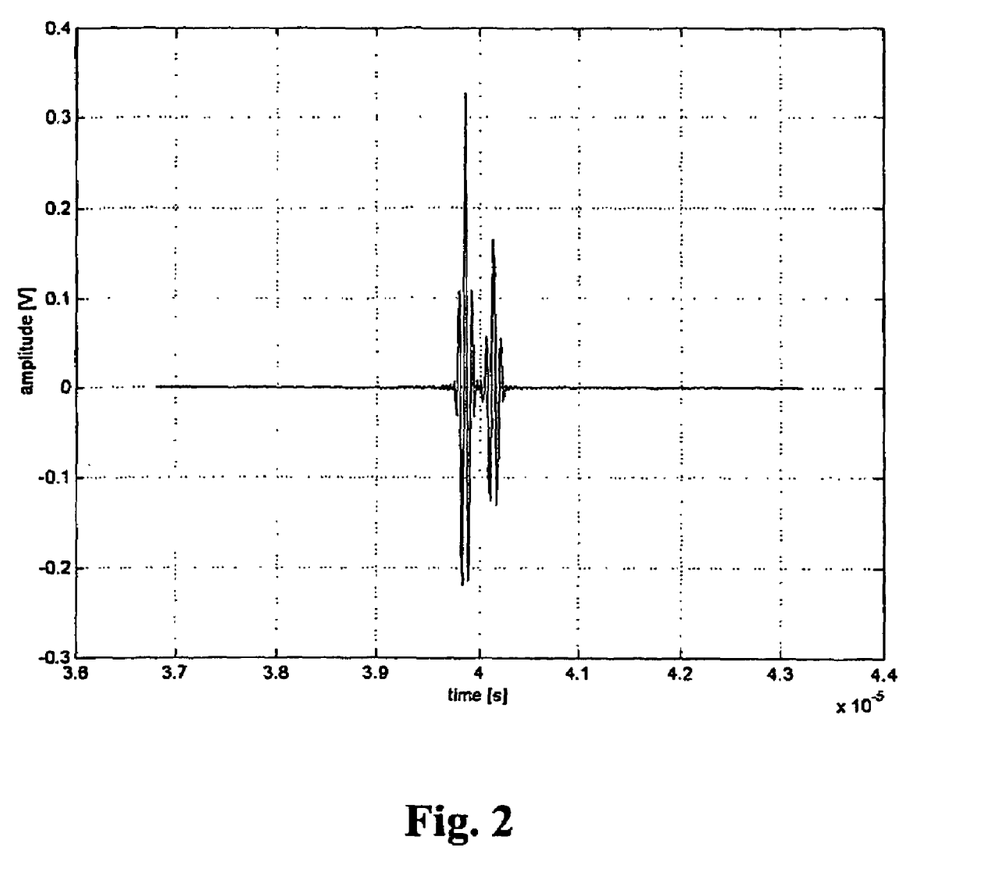
FIG. 2 is a representation of a reflected signal.

Interaction with the particles in the measuring beam 11, such as the particles 3 and 4 represented in FIG. 1, causes a reflected signal 6 which is registered or recorded by means of the transducer 7 which now functions as a receiver. Upon registration or recordal, the reflected signal 6, of which an example is shown in FIG. 2, is processed in the arithmetic unit 13 with the aid of arithmetic operations.

By choosing a specific time window within which reflected signals 6 are registered, it is possible to define a measuring volume. The time window is here related to the actuation signal 5, such that reflected signals 6 can only be registered after a pre-set time interval after actuation of the transmitter 7. The edges of the measuring volume 14 are determined by the size of the measuring beam 11 and by substantially spherical segment-shaped surfaces which are unequivocally coupled to the edges of the time window. When the measuring beam 11 has a Gaussian intensity profile, the area where the actuation signal 5 has decreased by 6 dB relative to the center of the beam is an indication of the width of the measuring beam 11. Only reflected signals that are caused by particles 3, 4 within this measuring volume 14 are registered.

For more extensive details regarding the measuring device, reference is made to the present applicant's earlier patent publication EP 0801305 A. In this publication, a method is described in which only information of a reflected signal 6 is processed with regard to the particle that causes the largest amplitude in the reflected signal 6. This is done by taking into account only specific information of the reflected signal 6, viz. the maximum amplitude of the signal 6.

Figure 7:
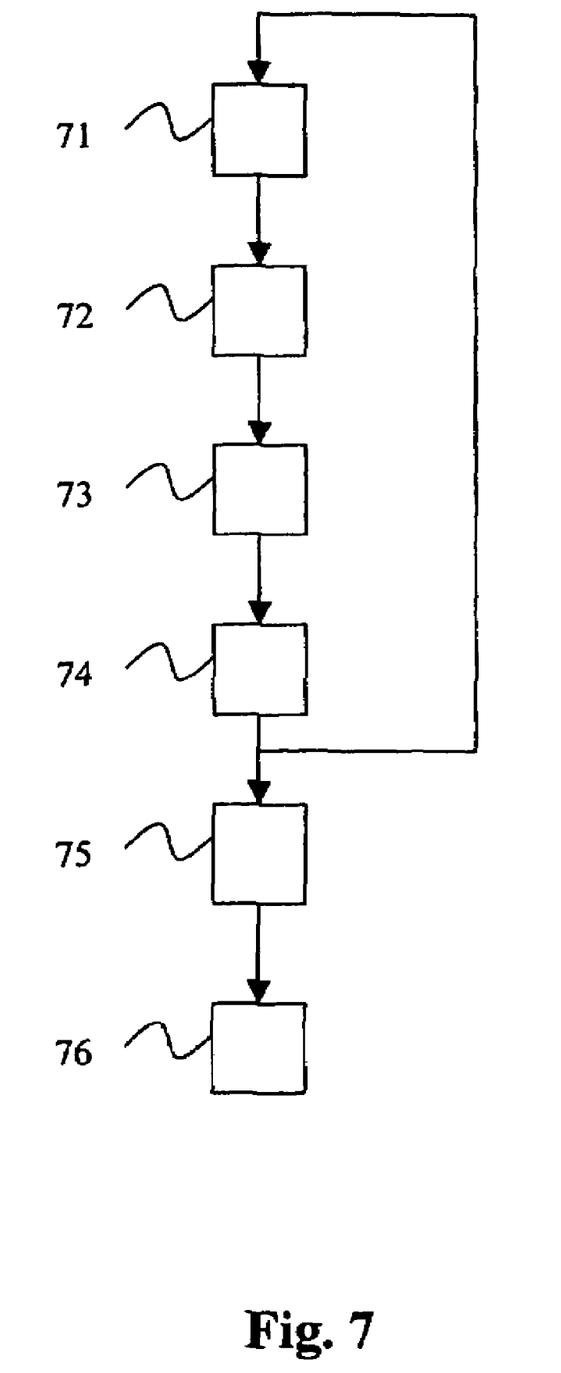
FIG. 7 is a flow diagram of the method according to the invention.

In the embodiment according to the invention, detection of more than one particle takes place by handling the reflected signal 6 in a different, more suitable manner. FIG. 7 shows a flow diagram according to the method of the invention. The steps of the method are described in more detail hereinbelow.

That after each initiation of a measurement (step 71) an actuation signal 5 is generated (step 72) and the reflected signal 6 is registered (step 73) in each measurement, has been addressed hereinabove. One embodiment of the invention is distinguished from existing, less accurate measuring methods by the following steps in the method.

Figure 3:
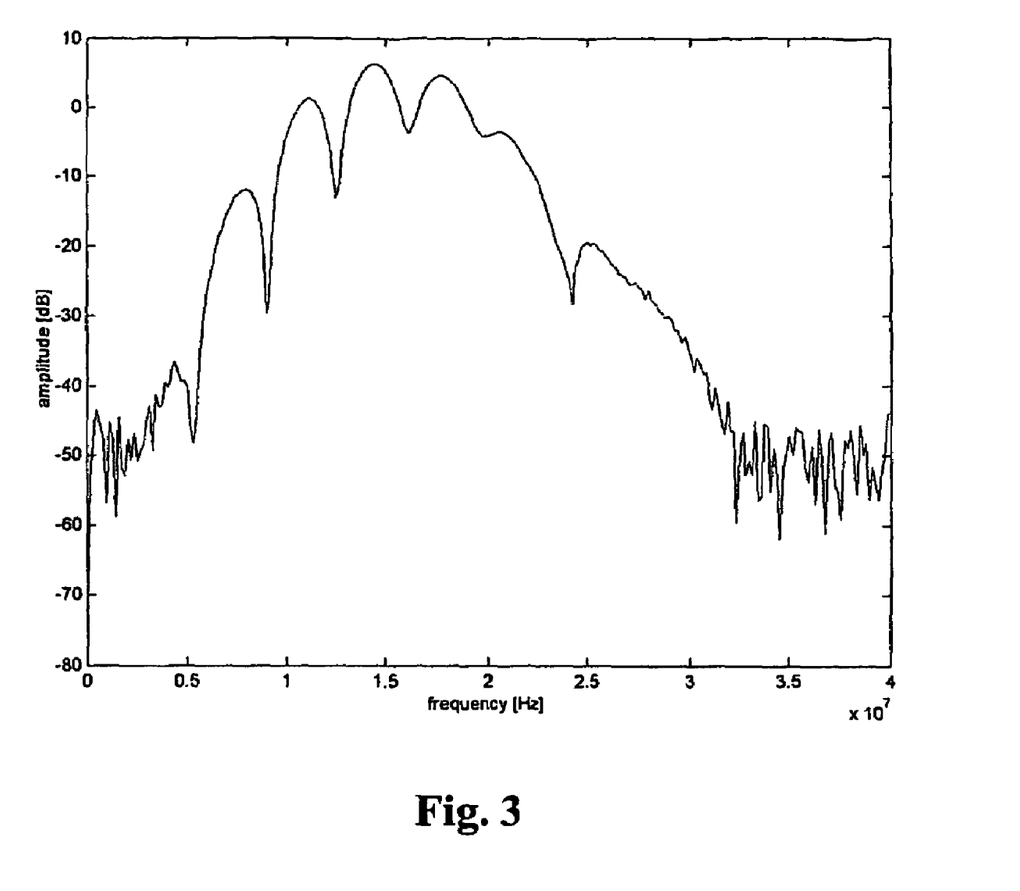
FIG. 3 is a representation of a power spectrum of a reflected signal.

Of a reflected signal 6, the arithmetic unit 13 determines the spectral counterpart of the reflected signal 6, using a discrete Fourier transformation. By squaring the modulus thereof, the power spectrum of the reflected signal 6 is obtained, which forms a first dataset and represents an autocorrelation function of the reflected signal 6 (step 74). An example of such a power spectrum is shown in FIG. 3. The power spectrum of the reflected signal 6 is a suitable representation of information with regard to reflections which have been caused by particles 3, 4 in the suspension 9.

Step 74 will be elucidated hereinbelow with the aid of a few formulae, it being assumed, for simplification, that each reflection of a particle 3, 4 in the suspension 9 causes an identically shaped reflected pulse s(t) as a function of time. When more than one particle 3, 4 make a contribution to a reflected signal 6, $$S(t) = \Sigma_i A_i s(t+\tau_i)$$

represents the reflected signal 6, wherein the index i sums over all pulses in the reflected signal, $A_i$ is the amplitude of a reflected pulse, and $\tau_i$ represents the time difference between the different pulses. The amplitude of each pulse in the reflected signal 6 depends on the intensity of the sound beam at the location of the particle that caused the pulse, and also on the size and the type of the particle. The time difference between the different pulses in the reflected signal 6 depends on the relative positions of the particles in the measuring volume with respect to the receiver 7.

Calculating an autocorrelation function $R(\tau)$ of the reflected signal 6 is represented in formulaic form as $$R(\tau) = \langle \sum_{i,j} A_i s(t+\tau_i) A_j s(t+\tau+\tau_j) \rangle_t$$

$$= \sum_i A_i^2 C_{i,i} + \sum_{i,j,i \neq j} A_i A_j C_{i,j},$$

wherein the terms between the straight brackets "< >" are integrated over a time interval. Further, $C_{i,j}$ represent autocorrelation terms of the pulses s(t) with themselves, while $C_{i,j}$ represent cross correlation terms of one pulse with another pulse in the reflected signal 6.

Calculating these first datasets (step 74) can be done after each measurement or after completing a whole series of measurements. Moreover, it is not necessary to determine a first dataset of each reflected signal 6, if it is chosen not to process the signal further, for instance due to the presence of an amount of significant noise.

In a next step of the method (step 75), subsequently the power spectra of a large number, for instance 100,000, reflected signals 6 are added up, so that a second, cumulated, dataset is obtained. When forming a representation of the sum of the first datasets, viz. the representatives of the autocorrelation functions, whereby the autocorrelation functions correspond with the reflected signals 6 from the measurements, the cross correlation terms $C_{i,j}$ make a significantly smaller contribution than the autocorrelation terms of the pulses s(t) with themselves $C_{i,i}$. This last is a result of the stochastic distribution of the time differences $\tau_i$ between the pulses in a reflected signal 6. With each reflected signal 6, the differences between the times at which the pulses start are uncorrelated with respect to the situation in another measurement. This is connected with the random positions of the particles relative to each other and relative to the transmitter 7 and the receiver 7. These positions are stochastically distributed and are different in each measurement, also called realization. Therefore the cross correlation between the different pulses, certainly with large numbers of measurements, averages out and the cross correlation terms do not make any significant contribution in the second, cumulated dataset. The advantageous result is that only the relevant information, viz. the correlation of the pulses s(t) with themselves, is preserved, and that a representation has come about of a linear combination of all pulses in the reflected signals 6, of which a first dataset has been determined.

In the reflected signals 6, particles of a given size that are situated at the edge of the sound beam yield a pulse of a smaller amplitude $A_i$ than particles of the same size that are situated in the center of the beam. When forming a representation of the sum of autocorrelation functions of the signals 6, another advantageous result arises in that for particles of a given diameter, only the average value of the squared amplitudes $A_i^2$ is of importance for the cumulated dataset. This is a consequence of the stochastic distribution of the particles in the sound beam, and the summation of a large number of individual signals. As a consequence, for particles of a given diameter, pulses reflected from any random position in the sound beam will be equally represented in the cumulated dataset. The contribution of these pulses in the cumulated dataset is determined by the number of these pulses, and the squared amplitude of these pulses averaged over all positions in the sound beam. The average squared amplitude can be calculated from the intensity profile of the sound beam.

Another advantage involved in the summation of the individual power spectra is the improvement of the signal-to-noise level of the cumulated dataset with respect to the signal-to-noise level of the individual reflected signal. This is a consequence of the fact that the information in the different individual signal is correlated, while the noise is uncorrelated. As a result, in a large number of measurements N, the amplitude of the cumulated signal is proportional to N, while the amplitude of the noise is proportional to the square root of N.

Figure 4:
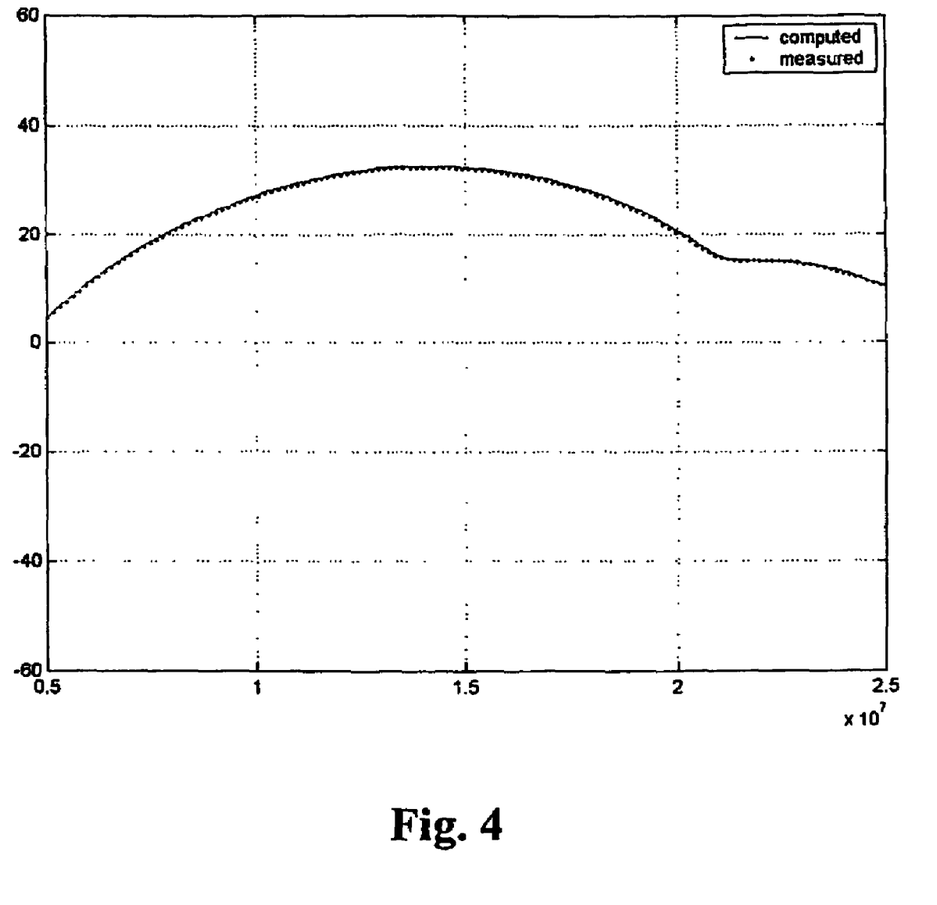
FIG. 4 is a representation of power spectra.

FIG. 4 (dotted line) shows an example of summed spectra.

Figure 5:
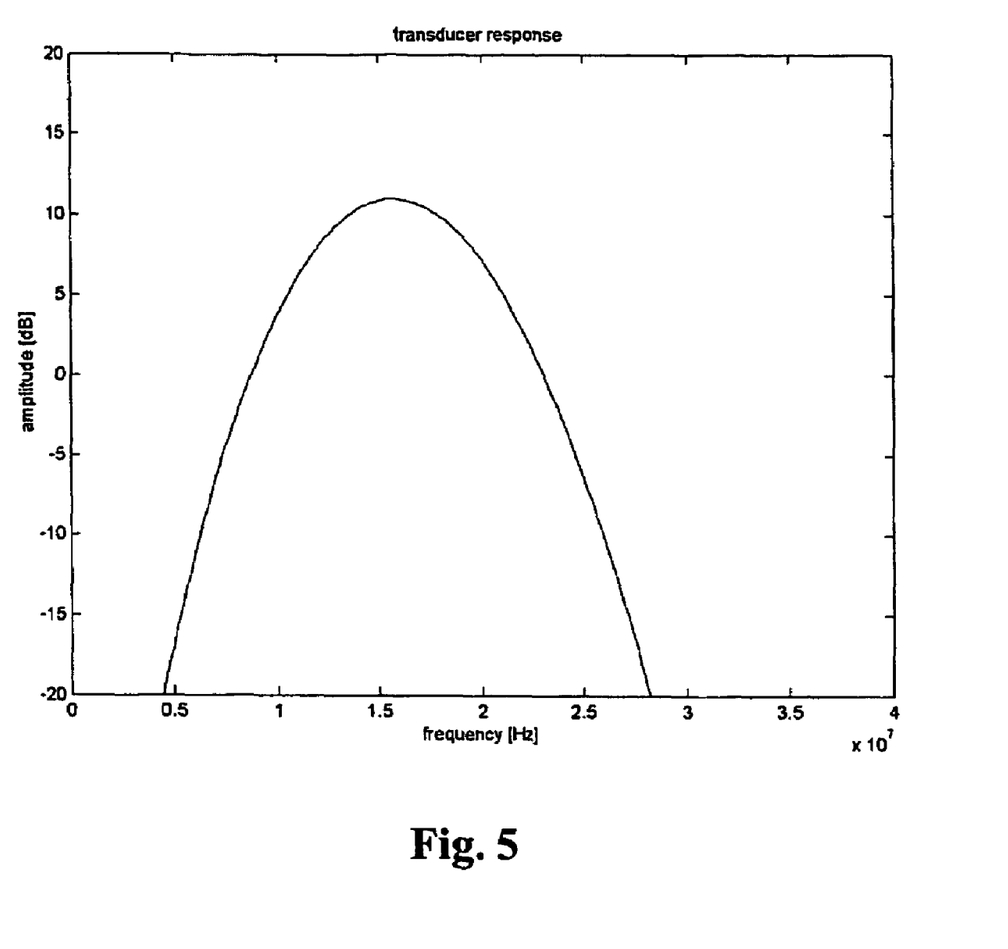
FIG. 5 is a representation of a transfer function of a transducer.
Figure 6:
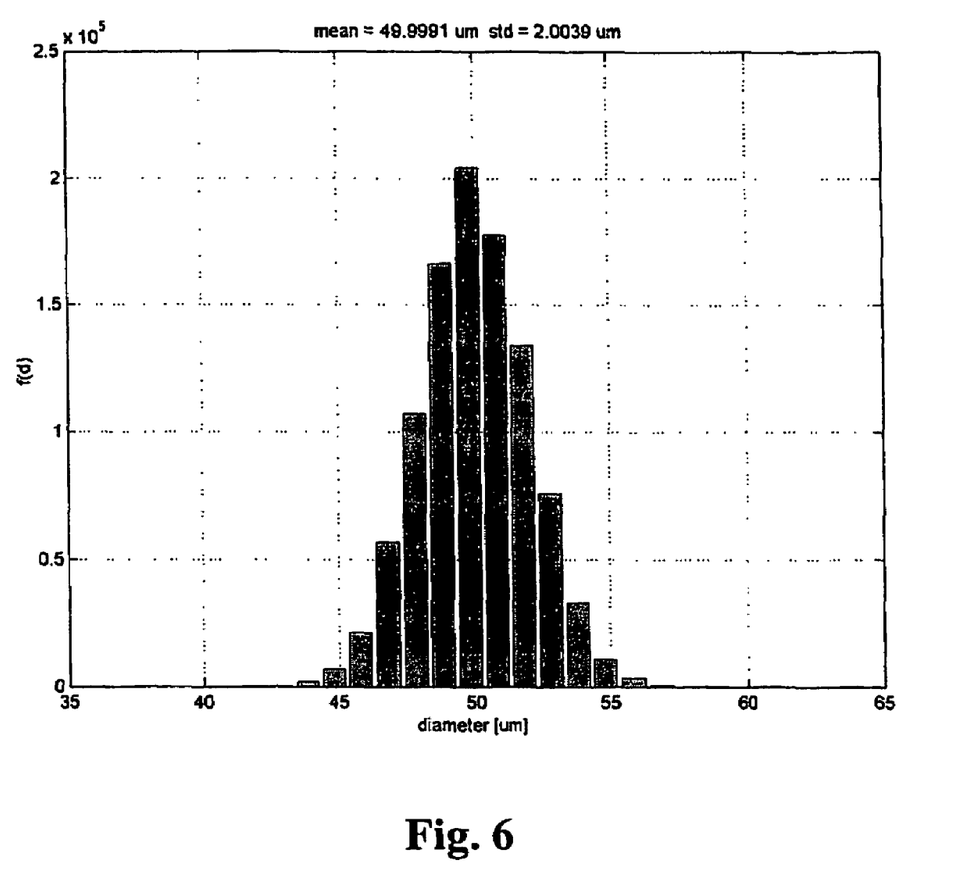
FIG. 6 is a representation of a particle size distribution.

The second, cumulated dataset, that is, the total power spectrum, is the starting point for the estimation of the particle size distribution (step 76). In the preferred embodiment, the arithmetic unit 13 solves the particle size distribution, which can take a form as shown in FIG. 6, from an analytical expression for the total power spectrum. In the preferred embodiment, this analytical expression is formed by the integral equation $P(f)=\int M(f,D)H(f)S(f)F(D)dD$, wherein P is the total power as a function of the frequency f. In the integrand, H represents the transfer function of the transducer 7, such as, for instance, shown in FIG. 5, and S is the power spectrum of the excitation signal with which the transducer is driven. M is a forward model for the power spectrum of the reflected signal (averaged over the intensity profile of the sound beam) as a function of the frequency f and the diameter of the particle D. An example of a forward model M of one such power spectrum is shown in FIG. 4 (continuous line). Finally, F represents the particle size distribution. The integration is performed, for instance, from D=0 to D=∞.

When several types of particles, for instance of different materials, are present in the suspension, the integral equation for the total power spectrum is formed by $P(f)=\Sigma_n(\int M_n(f,D)H(f)S(f)F_n(D)dD)$, wherein the index n sums over all types of particles. Here, $M_n$ represents a forward model for the power spectrum of the signal that has been reflected by particles of type n. The model $M_n$ is a function of the frequency f, the diameter D of the particle and the type n of the particle. $F_n$ represents the particle size distribution of the particles of type n.

All kinds of techniques known per se can be used to solve the particle size distribution F, or, if there are more types of particles, the particle size distributions $F_n$, from the integral equation for the total power spectrum. The particle size distribution F, or, if there are more types of particles, the particle size distributions $F_n$, are for instance solved from the integral equation for the total power spectrum by making use of a least squares method, known per se. To that end, the integral equation is discretized into the frequency f and the particle diameter D, resulting in an (overdetermined) matrix equation. In the case of more types of particles, for instance particles of different materials, this gives rise to a matrix of a block structure. In this equation, the unknowns are formed by the average values which the particle size distribution F, or in the case of different types of particles, the particle size distributions $F_n$, take on the diameter intervals such as these have been formed in the discretization of the integral equation. The matrix equation is solved numerically with standard solving methods. For extended description(s) of solving methods with regard to general matrix equations not specifically directed to above-described expressions, reference is made, for instance, to Chapter 3 of the book "Inverse Problem Theory, Methods for Data Fitting and Mode Parameter Estimation", Tarantola, A, 1987, Elsevier Science Publ.

Finally, the arithmetic unit 13 determines the particle concentration (for instance the mass or volume concentration) by integrating the particle size distribution over the particle size. According to the invention, an accurate estimation of the particle size distribution and the particle concentration is obtained, also when more than one particle 3 is present in the measuring volume 14 at the time of the measurement.

In this way, it is possible to obtain measuring results relatively fast on a suspension with floating particles therein. The measurements can be performed in-line and in-process. In contrast with optical measurements, this measuring method is moreover insensitive to pollutions on the transducer.

An application of the invention described lies, for instance, in the field of the oil industry, where it is important to determine the concentration of sand and oil contained in water that is being pumped up in the extraction of fossil fuels. Determining the concentration of oil in this water is not only important for environmental reasons, for instance for generating an alarm signal if the concentration exceeds a threshold value, but also for developing a strategy for recovering the fuels at a site.

Other applications can for instance be found in the field of medical laboratories, monitoring drinking water quality and controlling process parameters in the semiconductor industry.

The invention is not limited to the exemplary embodiment described here. Many variants are possible.

Thus, a different embodiment of the method is so arranged that of reflected signals as a function of time first datasets are determined in the form of autocorrelation functions. Thereafter, the thus obtained first datasets are combined into a sum for each time, thus yielding a cumulated autocorrelation function. In the handling of the signals, use is made here of the equivalence of the representation of the signals in the time domain and the frequency domain.

In another embodiment, the transmitter and the receiver are separate. This provides the advantage that both transducers can be optimized for their function, such as, for instance, a non-focused piezo transmitter or a strongly-focused PVDF receiver with a good reception efficiency and a focusing that is simple to construct. Also, the transducers can be so arranged that the properties could not, or difficultly so, be realized in the case of an integrated transducer. An example of this is a receiver which has a relatively high frequency range. Furthermore, the electronic control of the transducers can be made of simpler design. Moreover, in this way, a disadvantage is eliminated that occurs with integrated transducers, viz. that the transducer after transmitting an acoustic signal is not directly available for receiving a reflected signal as a result of post oscillation of the mechanical part of the transducer. By making the transmitter and the receiver of separate design, the transmission of an actuation signal is mechanically uncoupled from the measurement of a reflected signal, so that a higher repeat frequency of measurements is possible. Also, the measuring volume can be chosen to be closer to the transmitter and receiver. In addition, when a separate transmitter and receiver are placed at an angle relative to each other, the measurement of the reflected signal is not disturbed by multiple scatter between the transmitter and the particles in the suspension. This is especially of importance with relatively high concentration particles.

By including extra receivers in the wall of the channel, more information about the particles in the suspension becomes available if the scatter is non-uniform. In this way, it is possible, for instance, to determine particle size distributions as a function of the position in the channel or to construct a particle size distribution using fewer actuation signals. Moreover, the application of more than one transmitter or receiver permits a dynamic adjustment of the measuring beam, both as regards focusing and as regards beam shape, for instance for the purpose of the concentration of the particles in the suspension or the damping of the acoustic signals.

In another embodiment, the intensity distribution of the sound beam is not Gaussian, as, for instance, with a non-focused beam.

In yet another embodiment, the arithmetic unit 13 is integrated with the transducer 7.

In a still further embodiment, the integral equation is solved with the aid of a maximum likelihood method.

It will be clear that for practicing the invention, use can be made, among other things, of a generally applicable computer which comprises the arithmetic unit and which is programmed with a computer program designed for that purpose, for steps such as the calculation of the autocorrelation functions, or the power spectra representing these autocorrelation functions, calculating the cumulated correlation functions, or the cumulated power spectra representing these cumulated autocorrelation functions, and for solving the particle size distribution. Such computer programs can be supplied to the computer with all kinds of media, such as optical and magnetic disks, via Internet transmission, and so forth. A number of these calculations, of course, can also be performed with hardware especially intended for the purpose.

Similar and other variants will be clear to the skilled person and are understood to fall within the scope of the invention, as set forth in the following claims.

The invention claimed is:

1. A method for characterizing a suspension with particles floating therein, which method comprises the steps of:
    performing a plurality of measurements, wherein each of the measurements comprises:
        generating an acoustic actuation signal in the suspension using a transmitter, and
        registering an acoustic reflected signal coming from the suspension as a result of the actuation signal;
    calculating, for each of the measurements, a first dataset based on information obtained during the measurement of the corresponding reflected signal, wherein each of said first datasets contains information which represents an autocorrelation function of said corresponding reflected signal as a function of time;
    combining the first datasets into a second, cumulated dataset, which represents a sum of the autocorrelation functions from said first datasets;
    calculating a representation of a particle size distribution within the suspension from an expression representative of for the second, cumulated dataset; and
    outputting the representation of the particle size distribution to a user.

2. A method according to claim 1, characterized in that the calculation of the first dataset is by determining a power spectrum of the corresponding reflected signal.

3. A method according to claim 1, characterized in that the cumulated dataset is expressed by means of a matrix equation.

4. A method according to claim 1, characterized in that the particle size distribution is determined by solving the expression for the cumulated dataset using a least squares method.

5. A method according to claim 1, characterized in that the cumulated dataset is expressed in terms of particle size distributions of particles of different materials, and wherein the calculating further comprises calculating representations of the particle size distributions of the respective different materials from the expression of the cumulated dataset.

6. A method according to claim 1, characterized in that the method comprises the step of determining the particle size concentration in the suspension on the basis of the particle size distribution.

7. A device for characterizing a suspension with particles floating therein comprising:
- a channel for the suspension,
- a transmitter for generating an acoustic actuation signal in the suspension,
- a receiver for registering information representative of an acoustic reflected signal which comes from the suspension as a result of the actuation signal, and
- means for determining a particle size distribution in the suspension based on composite information registered at the receiver representative of a plurality of acoustic reflected signals which come from the suspension as a result of the transmitter generating a respective plurality of acoustic actuation signals, characterized in that said means is arranged for,
- calculating a first dataset for each of said reflected signals using the corresponding registered information, wherein each of the first datasets contains information which represents an autocorrelation function of said corresponding reflected signal as a function of time,
- combining the first datasets into a second, cumulated dataset, which represents a sum of the autocorrelation functions from said first datasets, and
- calculating a representation of the particle size distribution within the suspension from an expression representative of the second, cumulated dataset.

8. A computer program on a computer readable medium for characterizing a suspension with particles floating therein, on the basis of a registered acoustic reflection, which computer program contains instructions for causing the following steps to be executed:
- registering an acoustic reflected signal which comes from the suspension as a result of an actuation signal,
- determining a particle size distribution in the suspension based on information registered at the receiver and representative of a plurality of acoustic reflected signals which come from the suspension, characterized in that the determining the particle size distribution comprises the steps of:
- calculating a first dataset for each of said reflected signals based on the corresponding registered information, wherein each of the first datasets contains information which represents an autocorrelation function of said corresponding reflected signal as a function of time,
- combining the first datasets into a second, cumulated dataset, which represents a sum of the autocorrelation functions from said first datasets,
- calculating a representation of the particle size distribution from an expression for the second, cumulated dataset, and
- outputting the representation of the particle size distribution to a user.

* * * * *